United States Patent [19]

Burgert et al.

[11] Patent Number: 4,984,579
[45] Date of Patent: Jan. 15, 1991

[54] APPARATUS FOR TREATMENT OF SENSORINEURAL HEARING LOSS, VERTIGO, TINNITUS AND AURAL FULLNESS

[76] Inventors: Paul H. Burgert, 611 W. Harvard, Glenwood Springs, Colo. 81601; Richard L. Goode, 121 Giffen, Los Altos, Calif. 94022; Terry L. Burke, 404 Park Dr., Glenwood Springs, Colo. 81601

[21] Appl. No.: 383,078

[22] Filed: Jul. 21, 1989

[51] Int. Cl.$^5$ ............................................ A61B 15/00
[52] U.S. Cl. ................................... 128/747; 128/897; 128/898
[58] Field of Search ............... 128/400, 401, 746, 747, 128/897, 898

[56] References Cited

U.S. PATENT DOCUMENTS

| | | | |
|---|---|---|---|
| 3,000,271 | 9/1961 | Harvey et al. | 128/2.1 |
| 3,757,769 | 9/1973 | Arguimbau et al. | 128/2 Z |
| 3,882,848 | 5/1975 | Klari et al. | 128/2 Z |
| 4,009,707 | 3/1977 | Ward | 128/2 Z |
| 4,023,561 | 5/1977 | Servos | 128/2.1 R |
| 4,106,493 | 8/1978 | Proctor et al. | 128/2 R |
| 4,106,496 | 8/1978 | Proctor et al. | 128/2 R |
| 4,325,386 | 4/1982 | Katz | 128/733 |
| 4,466,438 | 8/1984 | Katz | 128/400 |
| 4,563,231 | 2/1971 | Ducote et al. | 128/2.1 |
| 4,688,582 | 8/1987 | Heller et al. | 128/746 |

Primary Examiner—Randall L. Green
Assistant Examiner—Randy Shay
Attorney, Agent, or Firm—John E. Reilly

[57] ABSTRACT

A portable apparatus for immediate self-treatment of sensorineural hearing loss, vertigo, tinnitus and aural fullness includes a probe for establishing a hermetic seal with the ear canal and a pump for establishing a positive or negative pressure in the ear canal via a hose connected to the probe. The portable apparatus further includes special controls accessible only to a physician or audiologist for establishing the maximum pump pressure and duration of operation optimal for the individual patient. The portable apparatus also includes controls accessible to the patient for initiating pump operation and varying the pump pressure and duration of operation within the limits established by the special controls. The apparatus includes its own independent power supply and may be conveniently carried anywhere by the patient so that it is with him at all times. Whenever the patient senses the onset of symptoms associated with sensorineural hearing loss, vertigo, tinnitus or aural fullness, he merely inserts the probe into the afflicted ear and, using the controls, activates the pump.

16 Claims, 1 Drawing Sheet

APPARATUS FOR TREATMENT OF SENSORINEURAL HEARING LOSS, VERTIGO, TINNITUS AND AURAL FULLNESS

The invention relates to a novel and improved method and apparatus for the treatment of symptoms such as dizziness, tinnitus, fluctuating hearing loss, aural fullness and visual fixation problems associated with endolympathic hydrops or Meniere's disease.

BACKGROUND AND FIELD OF INVENTION

Devices for studying afflictions associated with the ear are well-known. Typically, such devices irrigate the ear with a hot or cold fluid. For example, U.S. Pat. No. 3,563,231 to B. A. Ducote discloses a device for irrigating the ear canal with hot or cold water in order to induce nystagmus. Irrigation of the ear with various hot or cold fluids for studying or evaluation purposes is disclosed in U.S. Pat. Nos. 4,023,561 (to Proctor et al.), 4,106,493 (to Proctor et al.), 4,023,561 (to G. H. Servos) and 3,000,271 (to Harvey et al.).

Devices for treating or alleviating such afflictions by irrigating the ear with hot or cold fluids are disclosed in U.S. Pat. Nos. 4,325,386 and 4,466,438, both to Jay W. Katz. Such devices are disclosed as being portable for use by the patient.

The present invention concerns the treatment of afflictions of the ear by temporarily changing the pressure in the ear canal so as to alleviate Meniere's disease symptoms, such as, hearing loss, vertigo, tinnitus, nausea and aural fullness. This general approach is alluded to in the following publications: S. Ingelstedt et al., "Immediate Relief of Symptoms During Acute Attacks of Meniere's Disease Using a Pressure Chamber", *Acta Otolaryngolocica,* Volume 82, pages 368-378, (1976); 0. Densert et al., "Immediate Restoration of Basal Sensorineural Hearing (Meniere) Using a Pressure Chamber", *Acta Otolaryngologica,* Volume 80, pages 93-100 (1975); B. Densert et al., "Overpressure and Treatment of Meniere's Disease", *Laryngoscope,* Volume 92 (November, 1982); and O. Tjernstrom et al., "Hearing Improvement in Attacks of Meniere's Disease Treated with Pressure Chamber", *Adv. Oto-Rhino-Laryng.,* Volume 25, pages 54-60 (1979).

The treatments described in the foregoing publications of using induced pressure changes in the ear to alleviate symptoms of Meniere's disease is distinguished from well-known techniques of introducing a constant or fluctuating air pressure in the ear canal to measure the acoustic response of the ear. Such techniques are described in U.S. Pat. Nos. 4,688,582 (to Heller et al.), 4,009,707 (to J. W. Ward), 3,882,848 (to Klar et al.) and 3,757,769 (to Arguimbau et al.). For example, the patent to J. W. Ward mentioned here (U.S. Pat. No. 4,009,707) discloses an ear probe connected to a pump for the purpose of evacuating pressure in the ear to facilitate an acoustic impedance measurement. The ear probe maintains an air-tight seal with the ear canal while the pump pressure is regulated at a selected level using pressure regulating techniques well-known in the art.

Unfortunately, the approach of inducing a pressure change in the ear to alleviate Meniere's disease symptoms and the like suffers from a number of disadvantages. First, the use of a pressure chamber is highly inconvenient in that the patient must hasten to the nearest clinic having a pressure chamber whenever he senses the onset of such symptoms. In many cases, this is not only inconvenient but the patient may never reach the clinic before an episode of such symptoms has run its course. Secondly, each time the patient enters the pressure chamber for treatment, skilled personnel must be present to operate the chamber, representing a significant expense to the patient, as well as making immediate treatment dependent upon the availability of such skilled personnel at any hour of the day or night.

SUMMARY OF THE INVENTION

Accordingly, it is an object of the invention to provide a novel and improved portable device for automatically inducing an optimum pressure change in an individual patient's ear upon direct command from the patient.

It is a further object of the invention to provide such a device wherein the induced pressure may be preset so that the patient need make no adjustments to the device and need not remember or know his or her optimum pressure level.

It is yet another object of the invention to enable the patient to effect immediate self-treatment of symptoms such as sensorineural hearing loss, vertigo, tinnitus, aural fullness and the like without requiring the presence of skilled personnel.

A further object of the invention is to provide an inexpensive and conveniently portable device which may be controlled exclusively by the patient, if desired, for effecting immediate self-treatment of such symptoms as sensorineural hearing loss, vertigo, tinnitus, aural fullness and the like.

Yet another object of the invention is to facilitate the immediate self-treatment of sensorineural hearing loss, vertigo, tinnitus, aural fullness and the like by conveniently inducing a significant pressure change in the affected ear only without inducing a significant pressure change in any other part of the body.

A still further object of the invention is to provide an inexpensive portable apparatus which requires only the insertion of an ear probe to create an airtight seal within the ear and the actuation of an on/off switch by the patient, and nothing further, for immediate self-treatment whenever needed of sensorineural hearing loss, vertigo, tinnitus, aural fullness and the like through an induced pressure change in the outer ear whose magnitude and duration have been optimally predetermined by a doctor or audiologist for the individual patient.

In accordance with the present invention, an inexpensive portable apparatus which can be conveniently carried by the patient and activated when needed for the immediate self-treatment by the patient of such symptoms as sensorineural hearing loss, vertigo, tinnitus or aural fullness to induce a predetermined pressure change in the patient's ear for a predetermined duration or length of time. The apparatus includes an ear probe which is easily inserted into the afflicted ear by the patient so as to establish an airtight seal with the ear, an air pump or pressure source, a hose connecting the air pump with the ear probe and a control system.

In the control system, an on/off switch and an automatic pressurization switch operated by the patient activates the apparatus whenever desired. The control system also automatically controls the pressure induced by the pump and the duration of pump operation through preset controls accessible only to the patient's doctor or audiologist. Manual controls are additionally provided by which the patient himself may vary the pump pressure and duration of operation within the limits established by the preset controls. The control system further includes a quick pressure release switch accessible to the patient for relieving the pressure change induced in the ear by the pump whenever desired without having to remove the ear probe from the ear.

In carrying out the invention, the ear probe assembly may assume various embodiments. The ear probe may be supported by an earhook or by a headset, as desired. Further, the probe tip, which is preferably formed of a deformable material, is removably mounted on the end of the hose. This permits the patient to select from a variety of differently shaped probe tips the most comfortable and effective probe tip which may be mounted on the end of the hose and inserted into the ear.

DETAILED DESCRIPTION OF PREFERRED EMBODIMENT

Figure 1:
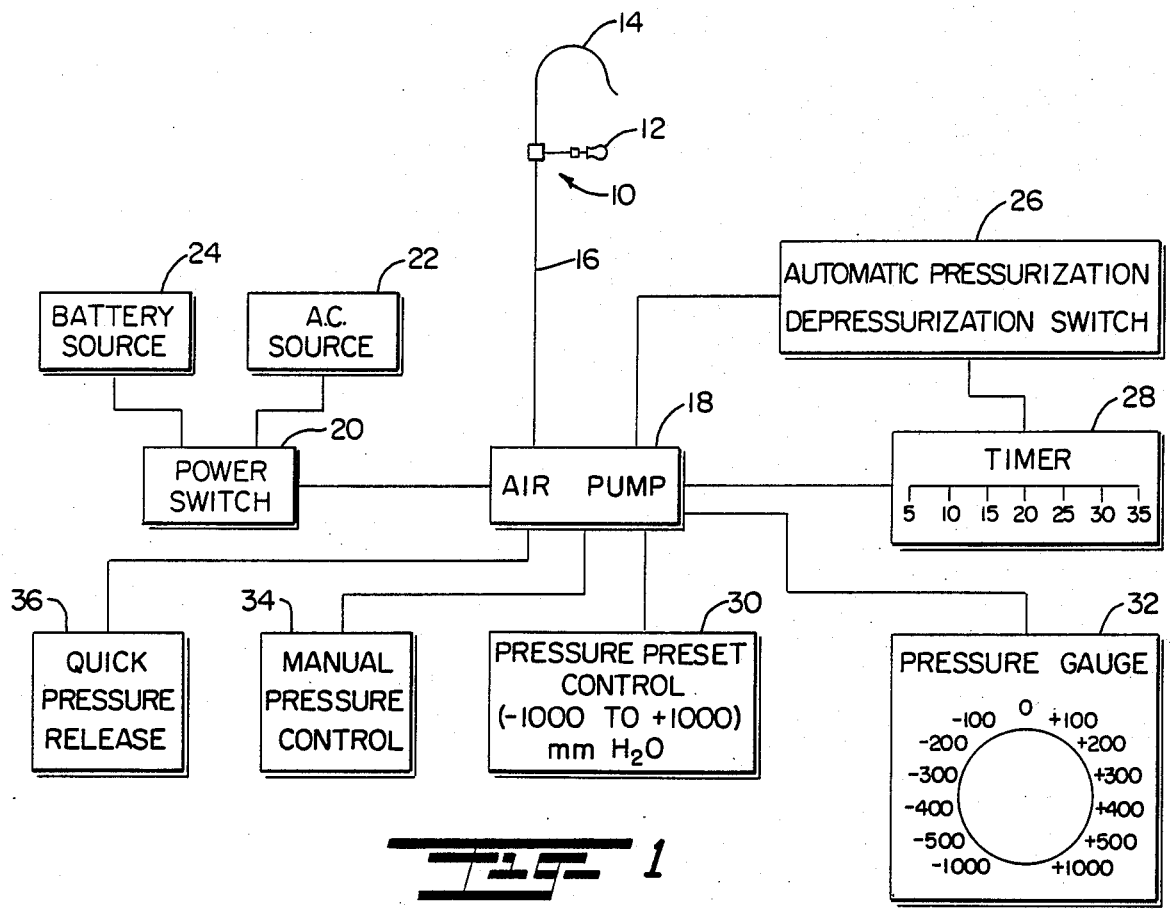
FIG. 1 is a block diagram illustrating the preferred embodiment of the invention.

Referring in detail to the drawings there is shown by way of illustrative example in FIG. 1 the apparatus of the invention which is compact and easily carried by the patient at all times. It is to be used by the patient during episodes of dizziness, tinnitus, fluctuating hearing loss and visual fixation problems which are associated with endolymphatic hydrops or Meniere's disease. The patient can activate the apparatus of FIG. 1 whenever he senses the onset of such symptoms for relief without needing assistance.

The apparatus of FIG. 1 includes an ear probe assembly 10 having a probe tip 12 which the patient inserts into the afflicted ear with the onset of one or more of the above-named symptoms so as to effect an air-tight seal with the ear. In the embodiment of FIG. 1, the probe assembly 10 is supported by an earhook 14 which the patient rests over his ear in a well-known manner. A hose 16 interconnects the probe tip 12 and an air pump 18, enabling the air pump 18 to pressurize the patient's ear canal so as to increase or decrease the pressure therein with respect to atmospheric pressure.

A control system governs operation of the air pump 18. The control system comprises a power switch 20 through which electrical power is supplied to the pump 18 from either an A.C. household electrical outlet source 22 or from a replaceable or rechargeable battery source 24 included in the portable apparatus of FIG. 1. After turning on the power switch 20, the patient activates an automatic pressurization/depressurization switch 26 to initiate operation of the air pump 18. The pressurization/depressurization switch 26 causes the air pump 18 to gradually pressurize the patient's ear until a predetermined pressure level is reached, to maintain that pressure level and then to depressurize the patient's ear after a predetermined time limit has been reached. The time limit is controlled by a timer 28. The timer 28 is synchronized to begin running for a predetermined duration when the pressurization/depressurization switch 26 is activated by the patient. As soon as the timer 28 has run to the end of its time limit, it will turn off the pressurization/ depressurization switch 26 thereby causing the pump 18 to depressurize the patient's ear until no pressure is exerted by the pump 18. At this point, the patient may turn off the power switch 20. Alternatively, means may be provided for automatically turning off the power switch 20 at this point.

The apparatus of FIG. 1 includes controls not generally accessible to the patient. Specifically, the time limit of the timer 28 is preset by the patient's doctor or audiologist to an optimum duration for the patient. Also, the pressure maintained by the pump 18 is determined by a pressure preset control 30 which is also not generally accessible to the patient. The pressure preset control 30 may be preset to regulate the pressure of the pump 18 at a particular level lying generally in the range of $-1000$ millimeters of $H_2O$ and $+1000$ millimeters of $H_2O$. Devices which regulate the pump pressure are well known in the art. The pressure preset control 30 permits the automatic pressurization/depressurization switch 26 to gradually increase the pump pressure to the desired pressure level, which may be either a positive or negative level with respect to the ambient pressure, whenever the switch 26 is activated by the patient; and, after the timer 28 runs out at the end of the predetermined time limit, to gradually decrease the pump pressure until the pump 18 exerts no pressure. Techniques well known in the art for the regulation and control of such an air pump, such as, those disclosed in U.S. Pat. No. 4,009,707, may be employed by the skilled worker in carrying out the present invention. In so doing, the invention may take the form of embodiments other than that illustrated in FIG. 1. For example, the pressurization/depressurization switch 26 may be connected to the pressure preset controller 30 and the timer 28 may be connected to the pressurization/ depressurization switch 26. As yet another possibility, all of the controls illustrated in FIG. 1 may be combined in a single electronic device designed especially for this purpose.

For most patients, the preferred pressure is typically $-500$ millimeters of $H_2O$ and the preferred time limit during which this pressure is held is 15 minutes. For assurance, a pressure gauge 32 is provided for verifying that the correct pressure is applied by the pump 18. The patient may manually vary the pressure applied by the pump 18 within the limit established at the pressure preset control 30 using a manual pressure control 34. A quick pressure release 36 enables the patient to immediately relieve the pressure applied to his ear whenever desired.

In addition to varying the pump pressure within the preset limit by means of the manual pressure control 34, the patient may vary the time duration during which air pressure is applied to his ear within the time limit established by the timer 28 by operating the manual pressure control 34 for a duration less than the time limit of the timer 28. Of course, the timer 28 will ultimately depressurize the system after reaching the preset time limit whether the pump 18 is controlled by the patient through the manual pressure control 34 or automatically through the automatic pressurization/ depressurization switch 26.

Figure 2:
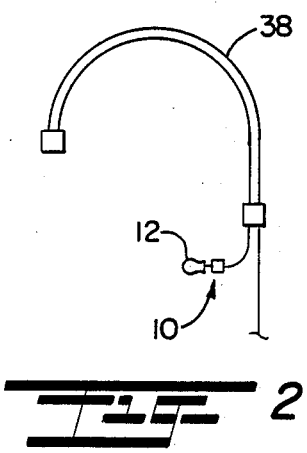
FIG. 2 is a diagram of an alternative embodiment of the ear probe assembly.

An alternative embodiment for supporting the ear probe assembly 10 using a headset 38, in lieu of the earhook 14, is illustrated in FIG. 2.

Figure 3:
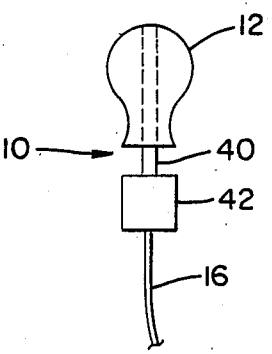
FIG. 3 is an enlarged view of the preferred embodiment of the probe tip assembly.

An enlarged view of the probe assembly 10 is illustrated in FIG. 3. The elastically deformable probe tip 12 receives a hollow stiff insert 40 which supports it. The insert 40 is in turn supported by a connector 42 which connects the insert 40 with the hose 16 and maintains an air-tight seal therebetween. Preferably, the elastic probe tip 12 is removable so that the probe tip may be properly fit for each patient, who may then select the most comfortable or effective probe tip.

The apparatus of the invention is used in association with one ear at a time, if it is necessary to treat both ears. In most cases it is necessary to treat only one ear, but in those cases where both ears are to be treated, the treatment may be performed sequentially.

In summary, the invention fills a great need and offers new advantages, as described above. While the invention has been described in detail with reference to the preferred embodiment thereof, it is understood that various modifications and changes may be made without departing from the spirit and scope of the invention as defined in the appended claims.

We claim:

1. A portable ear device for modulating air pressure in the ear canal of a patient which can be conveniently carried by the patient, comprising:
   an ear probe;
   air pressure changing means connected to said ear probe for inducing air pressure changes in the ear(s) of the patient;
   activating means for activating said pressure changing means;
   air pressure control means for controlling the pressure produced by said pressure changing means to produce a preset pressure level in said ear(s); and
   timer means for controlling the duration during which said pressure changing means produces said pressure at the preset pressure level in the ear(s) upon said pressure changing means being activated.

2. The portable device of claim 1 wherein said control means includes timer means for controlling the duration during which said pressure changing means produces said pressure change upon said pressure changing means being activated.

3. The portable device of claim 1, said air pressure control means causing said pressure to gradually change from an ambient level to said preset pressure level in response to said pressure changing means being activated and gradually changing said pressure from said preset pressure level to an ambient level upon expiration of said preset time duration.

4. The portable device of claim 1, said air pressure control means and said timer means being readily accessible only to skilled personnel and said preset pressure level and said preset time duration being set by skilled personnel prior to use by said patient for relief from symptoms included in a group of symptoms associated with endolymphatic hydrops or Meniere's disease.

5. The portable device of claim 4 wherein said pressure changing means is a pump, said switch means comprises a power switch for connecting said pump to a battery or an electrical power supply and an automatic pressurizer/depressurizer switch connected to said pump, said timer means comprises a presettable timer connected to said pump and said regulator means comprises a presettable pressure controller connected to said pump, whereby said pressurizer/depressurizer switch activates said pump, said timer begins running upon said pump being activated and said pressurizer/depressurizer switch deactivates said pump in response to said timer running for said preset time duration.

6. The portable device of claim 4 further comprising a manual controller accessible to said patient for manually varying said pressure and said time duration as desired so as not to exceed said preset pressure level and said preset time duration, respectively.

7. The portable device of claim 4 further comprising a pressure relief switch connected to said pump and accessible to said patient for immediately reducing to an ambient level the pressure applied by said pump.

8. The portable device of claim 1 wherein said control means is capable of maintaining said pressure at a preset level lying in a continuous range of positive and negative pressures between $-1000$ millimeters of $H_2O$ and $+1000$ millimeters of $H_2O$.

9. Portable apparatus facilitating immediate self-treatment by a person of any one of a group of symptoms associated with endolymphatic hydrops or Meniere's disease, said apparatus comprising:
   probe means insertable into an ear of said person for establishing a hermetic seal with said ear;
   pump means connected to said probe means for applying a predetermined pneumatic pressure to said ear;
   control means activatable by said person for causing said pump means to apply the predetermined pressure to said ear; and
   timer means for controlling the duration during which said pump means maintains the predetermined pressure.

10. The apparatus of claim 9 further comprising a portable power source connected to said pump means, said control means comprising means accessible to skilled personnel for setting said predetermined pressure and said predetermined time duration in accordance with the needs of said person.

11. The apparatus of claim 10 wherein said control means further comprises means accessible to said person for selectively reducing the pressure applied by said pump means from said predetermined pressure and for reducing the duration of the operation of said pump from said predetermined duration of time.

12. A method of treating an ear of a person afflicted with Meniere's disease by employing a portable air pressurization unit including an ear probe, air pressure changing means connected to the ear probe, activating means for activating the pressure changing means, presettable pressure control means for controlling the pressure produced by the pressure changing means, and timer means for controlling the time duration during which the pressure changing means produces a pressure at a preset pressure level when said pressure changing means is activated, said method comprising:
   providing a portable apparatus comprising:
      an ear probe;
      air pressure changing means connected to said ear probe for inducing air pressure changes in the ear(s) of the patient;
      activating means for activating said pressure changing means;
      air pressure control means for controlling the pressure produced by said pressure changing means to produce a preset pressure level in said ear(s); and
      timer means for controlling the duration during which said pressure changing means produces said pressure at the preset pressure level in the ear(s) upon said pressure changing means being activated; and
   using the portable apparatus to:
      (a) establishing a pressure level in the ear canal of said person for alleviating the symptoms of said disease;

(b) presetting said presettable control means at the pressure level predetermined in step (a);

(c) effecting a seal between said portable air pressurization unit and said ear canal at the onset of said symptoms associated with said disease by placing said ear probe in sealed relation to the ear canal;

(d) activating said pressure changing means for introducing air under a positive or negative pressure from said portable air pressurizer unit into said ear canal at a certain pressure not exceeding said predetermined pressure level and activating said timer means for maintaining that pressure for a certain time; and (e) regulating said air pressure control means for depressurizing said ear canal upon expiration of said certain time.

13. The method of claim 12 wherein said predetermining step (a) further comprises establishing a predetermined time duration for applying said predetermined pressure level to the ear of said person for alleviating said symptoms, and wherein said presetting step (b) further comprises presetting said presettable control means at the time duration predetermined in step (a).

14. The method according to claim 13 wherein said predetermining and presetting steps (a) and (b) are carried out by skilled personnel such as a physician and wherein said pressurizing and depressurizing steps (d) and (e) are carried out automatically by said portable air pressurization unit upon said control system being activated by said person.

15. The method according to claim 12 wherein said pressurizing step comprises pressurizing said ear canal by gradually increasing or decreasing the pressure from an ambient level to said certain level, and wherein said depressurizing step comprises depressurizing said ear canal by gradually returning said pressure from said certain level to an ambient level.

16. The method according to claim 12 further comprising setting said certain pressure to a value not exceeding said predetermined pressure level and setting said certain time to a value not exceeding said predetermined time duration.

* * * * *